United States Patent [19]

Welch

[11] Patent Number: 4,688,435
[45] Date of Patent: Aug. 25, 1987

[54] SYPHONING SAMPLER

[75] Inventor: Phillip J. Welch, Knutsford, England

[73] Assignee: British Nuclear Fuels plc, Warrington, England

[21] Appl. No.: 860,037

[22] Filed: May 6, 1986

[30] Foreign Application Priority Data

May 16, 1985 [GB] United Kingdom ............. 8512377

[51] Int. Cl.⁴ .............................................. G01N 1/14
[52] U.S. Cl. ............................. 73/864.34; 73/864.74; 73/863.86; 141/67; 137/145
[58] Field of Search .......... 73/863.83, 863.84, 863.86, 73/864.73, 864.74, 864.34, 864.35, 864.51, 864.63; 141/67; 137/145

[56] References Cited

U.S. PATENT DOCUMENTS

| 2,995,037 | 8/1961 | Parker et al. .................... 73/864.35 |
| 4,450,730 | 5/1984 | Levos et al. ...................... 73/864.61 |
| 4,512,203 | 4/1985 | Calame-Lonjean et al. .... 73/864.34 X |
| 4,516,436 | 5/1985 | Conche et al. ............... 73/863.85 X |

Primary Examiner—Tom Noland
Attorney, Agent, or Firm—William R. Hinds

[57] ABSTRACT

Sampling apparatus has a syphon with a longer arm (19) leading to a needle sampling station (20) from which extends a shorter arm (21) of the syphon. Liquid flow structure including a reverse flow diverter (10) is used to produce forward and reverse flow in the syphon and, on reverse flow, reduced pressure at the needle is produced by the head N of liquid, and during reverse flow some liquid enters a sampling bottle (24) through the needle (22). The needle extends into a T-piece and has a lower end at or below the mid line of the lateral leg of the T.

4 Claims, 6 Drawing Figures

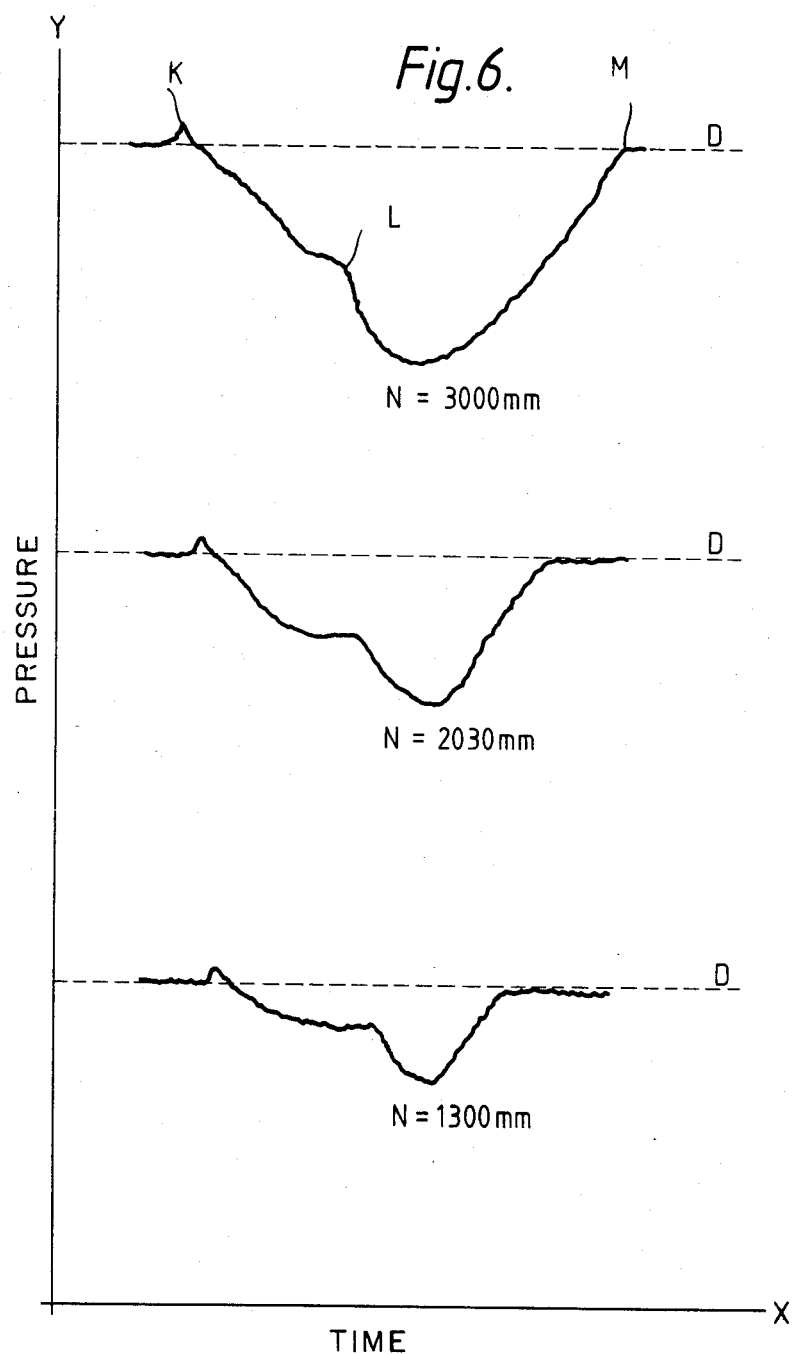

SYPHONING SAMPLER

BACKGROUND AND SUMMARY OF THE INVENTION

This invention relates to sampling.

This invention concerns a sampling apparatus comprising a source of liquid to be sampled, a sample station elevated with respect to the source, a first pipe for delivery of liquid from the source to the sampling station, a second pipe extending from the sampling station, the first and second pipes respectively forming longer and shorter arms of a syphon, a needle at the sample station having one end in a flow connection between the first and second pipes, a bottle at the sample station for receiving sample liquid through the needle, and means for causing delivery and return flows of liquid in the first pipe from the source to the sample station so that on the delivery flow liquid flows past the one end of the needle to the second pipe to reduce the pressure in the bottle and on the return flow a syphon effect is created and liquid flows from the second pipe past the one end of the needle to the first pipe and sample liquid flows through the needle into the bottle. The means for causing delivery may comprise a reverse flow diverter and means for operating the reverse flow diverter.

There may be a T-piece connection at the sampling station, the leg of the T being connected to receive liquid delivered to the station, one branch of the T being connected to the second pipe, and the other branch being closed by a plug through which the needle extends, said one end of the needle in the T-piece being at or below the level of the centre line of the leg.

The length of needle in the T-piece may have a greater internal diameter than the needle in the bottle.

BRIEF DESCRIPTION OF THE DRAWING

The invention may be performed in various ways and two specific embodiments with possible modifications will now be described by way of example with reference to the accompanying drawings, in which:

FIG. 6 shows curves of pressure against time.

DESCRIPTION OF THE ILLUSTRATED EMBODIMENTS

Figure 1:
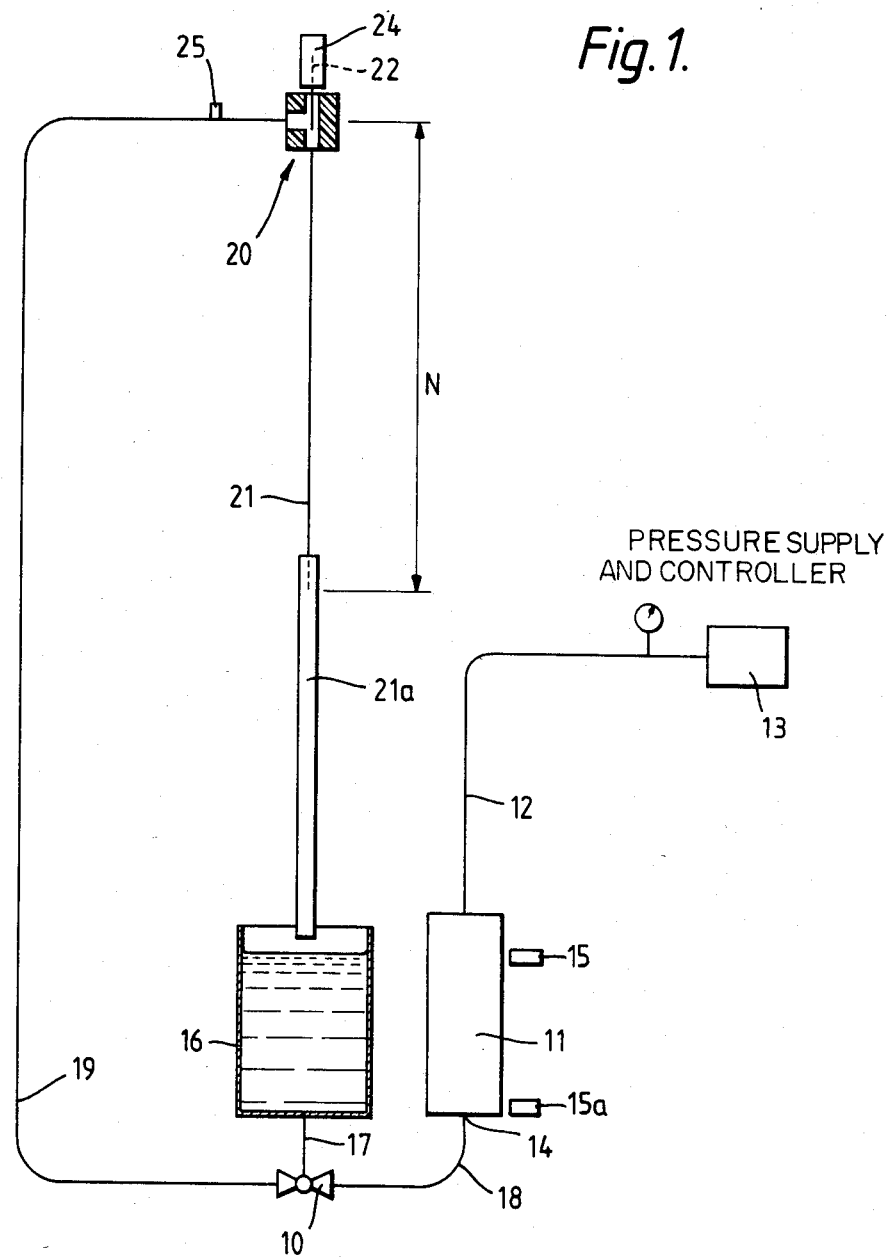
FIG. 1 is a sampling apparatus.

Referring to the drawings, pulsed flow from a Reverse Flow Diverter (RFD) is used to supply active liquor to a sample station and, in the liquor back-syphon stage of the cycle of operation, initially evacuate a sample bottle and ultimately draw liquor into the bottle. The advantages of this system are that liquor hold-up at the sample point is negligible, the system could be part of an RFD-fed liquor transport line, and only very short lengths of capillary making up the needle are necessary. In some cases the needle, when not fitted with a sample bottle, is not above atmospheric pressure when liquor is present. A reverse flow diverter comprises two opposed passages which diverge as they extend away from a chamber, and at least one transverse passage leading to the chamber.

The arrangement of an RFD-fed sample point is shown in FIG. 1. The operating cycle of the RFD 10 is such that on the drive stroke, the charge vessel 11 is pressurized with compressed air through line 12 from supply 13 including a timer until the liquor level in the charge vessel 11 is driven down to a position just above the outlet 14. Liquor is forced through the RFD; the input side of the RFD increases the velocity and reduces the pressure of the liquid and the output side recovers the pressure. During the drive part of the cycle, the pipework 19 from the RFD 10 up to the sample point 20, and the pipework 21 from the sample point back to the feed tank, are filled with liquor and the arrangement of a sample needle 22 with respect to a sample 'Tee' piece 23 is such that a sample bottle 24 is partially evacuated, because of flow from pipe 19 to pipe 21 causing reduced pressure in the needle, and is never pressurized. After a predetermined but adjustable time controlled by control 13 the pressure air in pipe 12 is vented and liquor flows back into the charge vessel 11 via run-back through line 19 and RFD 10 and also from tank 16 via lines 17, 18. During the part of the cycle when the charge vessel is venting and filling with liquor, back-syphoning occurs with the direction of liquor flow past the sample point being reversed (i.e. from pipe 21 to pipe 19) from that in the drive part of the cycle. At the onset of back-syphoning, the pressure at the sample point is at a reduced value corresponding to the head N of liquor in pipe 21 i.e. decreases to a minimum and further evacuation of the sample bottle occurs, but as back syphoning continues pressure at the sample point increases because the liquor head N decreases and eventually some liquor passing the needle 22 is drawn through the needle into the sample bottle 24. In general several cycles would be necessary to obtain the required sample volume. The pipe 21 forms a shorter arm of the syphon and pipe 19 a longer arm of the syphon.

With no sample bottle on the needle, any depression is destroyed and air inleakage permits the pipework to drain normally by breaking the syphon. A pressure transducer 25 is used to monitor pressure variations in delivery line 19. The vessel 11 may be vented manually. The cycle could be controlled by liquor level sensors 15, 15a responsive to level in tank 11 and arranged to cause venting or pressurising of tank 11 as the level reaches lower and upper limits.

Some examples are now given. With pipes, 19, 21 at 25 mm internal diameter (ID), pipe 21a of 75 mm ID and total length of discharge pipe 21, 21a, and a needle 22, 22a of 128 mm length and 0.85 mm ID extending to position C FIG. 2 and an RFD drive time of 5 sec, the graphs (a) (b) (c) RFD drive pressure (x axis) v sample rate ml/stroke of RFD (y axis) is shown in FIG. 3 for discharge pipe lengths of (a) 3000 mm (b) 2030 mm (c) 1300 mm, the height between the RFD 10 and the sample T-junction 20 being 5400 mm.

The RFD drive time was varied for condition (b) to give the results of Table 1:

TABLE 1

| SAMPLING RATE FOR VARIOUS RFD DRIVE TIMES | | | | |
|---|---|---|---|---|
| Length of Discharge Pipe from Sample 'Tee' mm (N in FIG. 1) | | 2030 | | |
| RFD Drive Pressure mbar | | 758 | | |
| Sample Needle Position | | C | | |
| RFD Drive Time sec | 3 | 3.5. | 4 | 5 |
| Maximum Vacuum in Sample Bottle mbar | 166 | 270 | 291 | 289 |
| Maximum Vacuum at 'Tee' mbar | 165 | 303 | 312 | 310 |
| Sample Rate ml/stroke of RFD | 0.4 | 1.4 | 1.5 | 1.5 |

Figure 2:
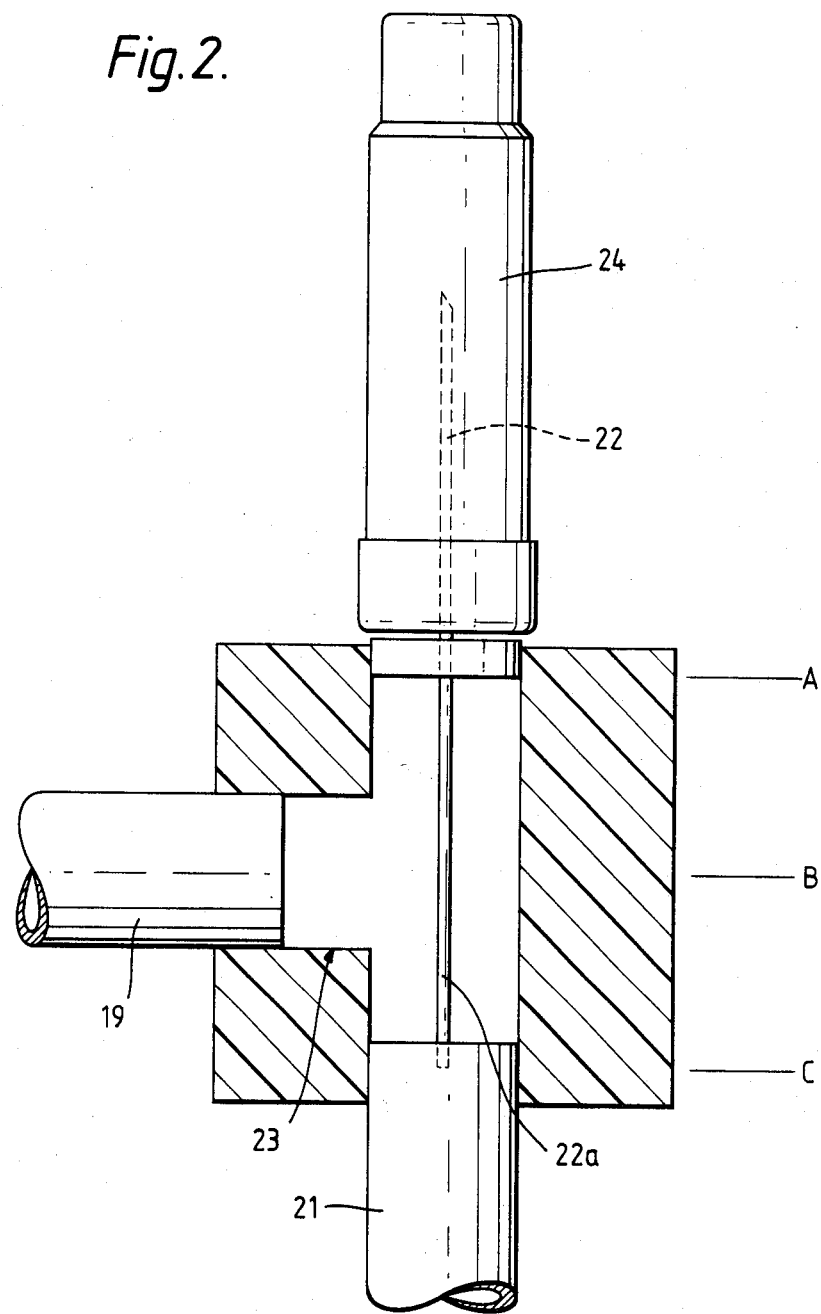
FIG. 2 is a part of FIG. 1 on an enlarged scale.
Figure 3:
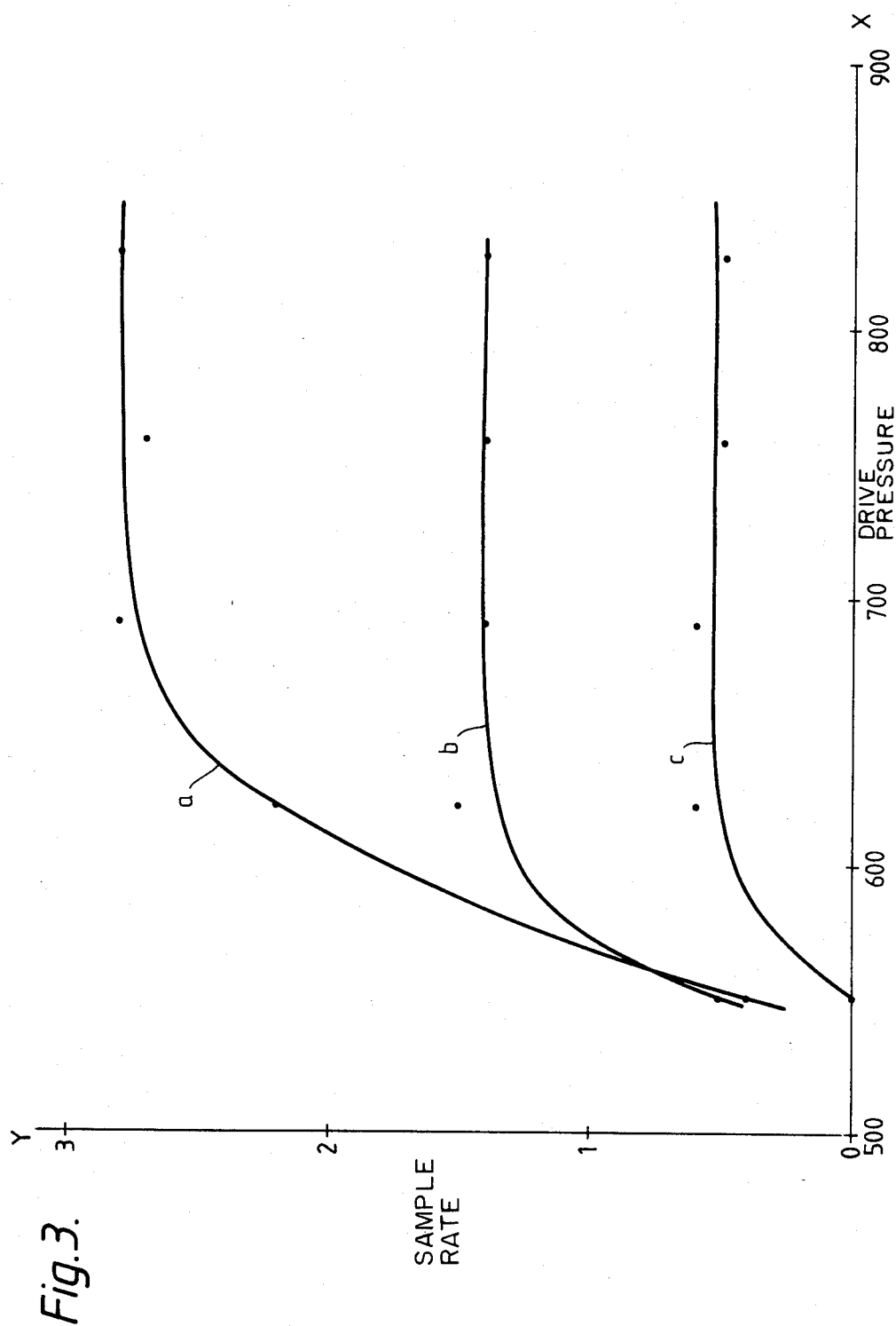
FIG. 3 is graphs of drive pressure v sample rate.
Figure 4:
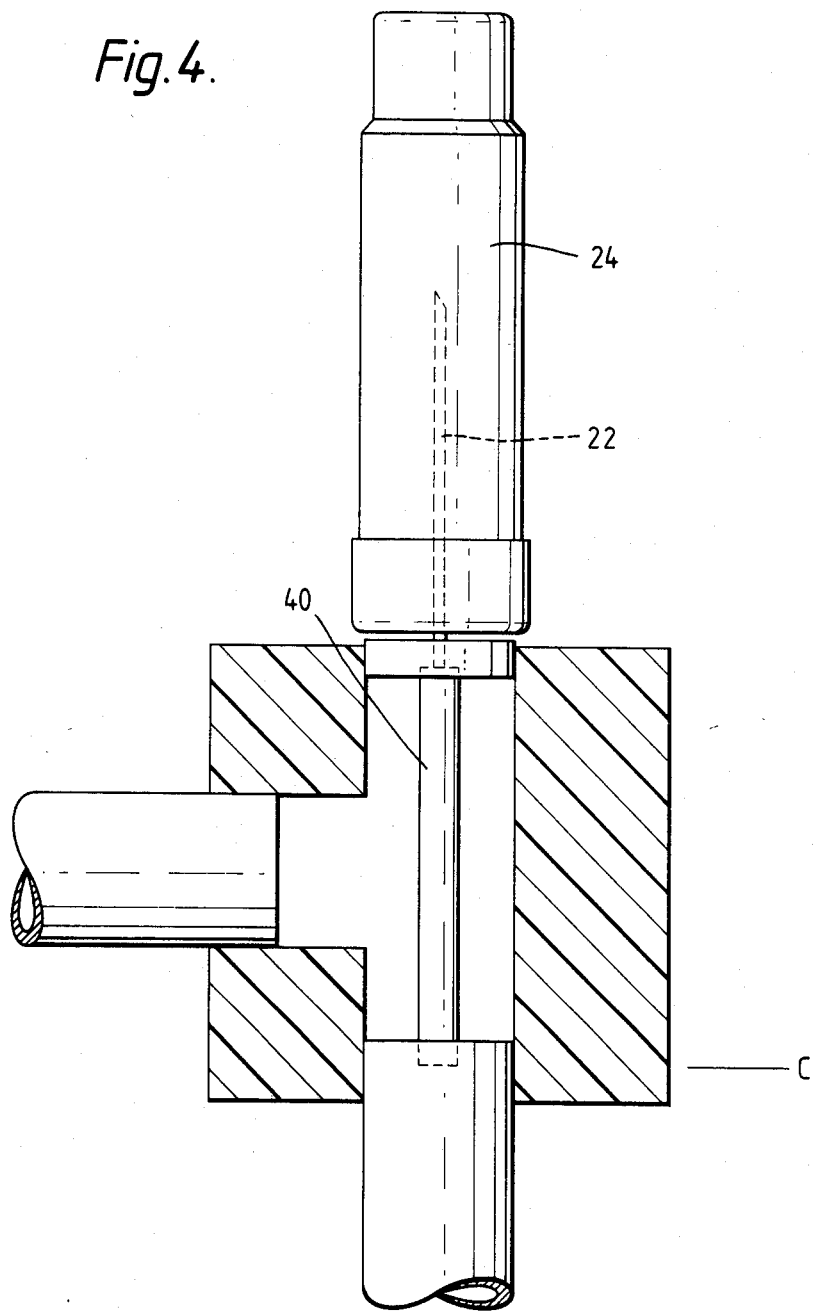
FIG. 4 is a modification of FIG. 2.

FIG. 4 shows a modified T-junction where the needle 22 is 60 mm long and 0.85 mm ID by 1.24 mm OD with an extension 40 of 75 mm length and 6 mm ID extending to position C, below the centre line B of pipe 19 (FIG. 2). Results obtained are shown in Table 2.

TABLE 2

| RFD Drive Time sec | 5 | | | | | |
|---|---|---|---|---|---|---|
| RFD Drive Pressure mbar | 483 | 551 | 621 | 690 | 758 | 827 |
| Maximum Vacuum in Sample Bottle mbar | 0 | 239 | 239 | 251 | 250 | 239 |
| Sample Rate ml/Stroke of RFD | 0 | 2.9 | 3.2 | 3.2 | 3.2 | 3.1 |
| Liquor Flow Rate Through Sample 'Tee' ml/sec | 116 | 252 | 524 | 491 | 522 | 494 |

Figure 5:
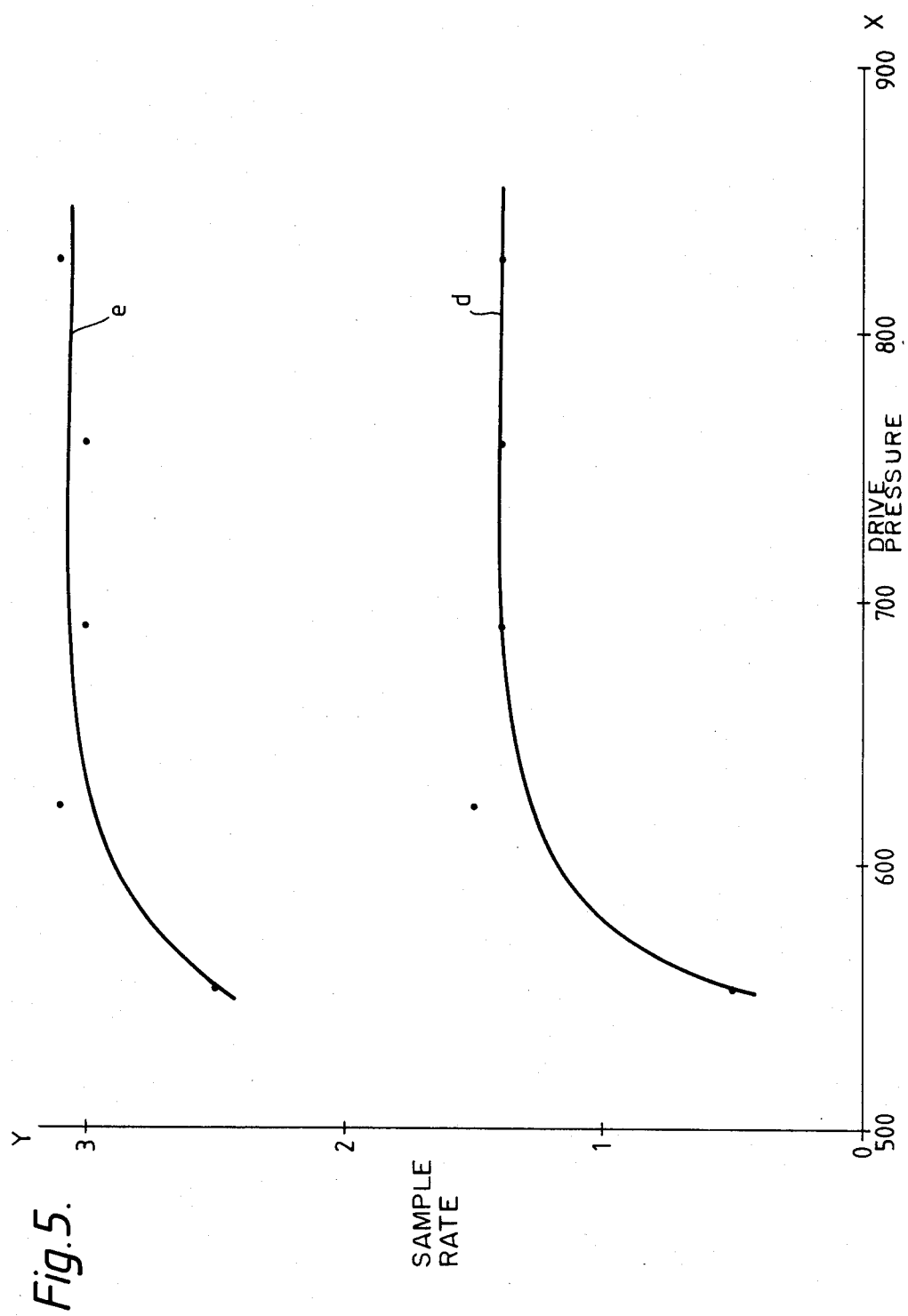
FIG. 5 is graphs of drive pressure v sample rate.

FIG. 5 shows graphs of sample rate ml/stroke of RFD (y axis) v RFD drive pressure (x axis) for the needle arrangement of FIG. 2 (graph d) and FIG. 4 (graph e).

For reasonable results the lower end of the needle 22 or extension 40 should be at or below the level B of the mid-line of pipe 19.

It is evident that the vacuum generated in the sample bottle 24 and the sampling rate both increase, with increasing length of discharge line 21 (N in FIG. 1) from the sample 'Tee' 20 and also with increasing RFD drive pressure up to 650 mbar, further increases in RFD drive pressure failing to increase sample rate. It should be noted that this RFD drive pressure is specific to the pipe geometry tested and different relationships may apply to other pipe arrangements. The vacuum generated in the sample bottle is substantially independent of the point at which the needle terminates within the sample 'Tee'; however the sample rate is greatest when the needle terminates below the center line of the side branch arm 19 of the angle 'Tee'. From Table 1 it is evident that the liquor sample rate is increased as RFD drive time is increased up to a time when the discharge pipework from the sample 'Tee' runs full of liquor; in this geometry, 3 sec. Further increase in drive time did not improve the sample rate.

In all cases when the needle terminated at positions A or B, of FIG. 2, air was ejected from the needle at some time during the RFD drive stroke. Air is ejected for a short period only as the liquor first arrives but then air flow is reversed and air is drawn into the liquor stream. This is caused by the general pressure fluctuation at the sample tee which takes the form shown in FIG. 6. In FIG. 6 the y axis is pressure, the x axis is time; the RFD drive time was 5 sec, the RFD drive pressure 758 mbar, needle position C. The points on the graphs are K: initial slight increase in pressure; L: end of RFD drive stroke and start of back stroke; M: end of back syphon, dotted lines D indicate atmospheric pressure. However, in considering the pressure curve for the needle it must be remembered that pitot effects cause a general reduction in the pressure in the needle provided the end of the needle is in such a position as to allow pitot effects to work. Thus when the needle is at or below the center line of the side arm of the tee then pitot effects prevent a positive pressure occurring in the needle. However, when the needle terminates above the center line of the side arm no pitot effects are present and the small "blip" of positive pressure recorded causes liquor or air to be ejected from the needle. When a short time later the pressure goes negative air is then drawn into the liquor stream. With the needle terminating at position C, of FIG. 2, no air or liquid was ejected at any condition.

Use can be made of the pressure transducer 25 sited in the RFD delivery line adjacent to the sample 'Tee' to prove a trace of pressure and vacuum during each complete stroke of the RFD. Typical forms of the trace are shown in FIG. 6 where it is evident that, with the configuration tested, as liquor reaches the transducer 25 a very small positive pressure pulse is seen, the pressure then rapidly becomes subatmospheric. At the end of the RFD drive stroke and the commencement of the back syphon the pressure reduces still further to a minimum and then returns to atmospheric. It is suggested that a similar situation exists in the sample bottle.

Thus, the length N of pipework 21 on the discharge side of the sample 'Tee' 20, returning to the feed tank, influences the sample rate since it determines the length of time that liquor is available at the sample needle 22 during the back syphon part of the cycle. However, excessive lengths of discharge pipe could produce high pressure at the sample 'Tee', during the RFD drive stroke, with the danger of liquor ejection from the needle. High pressures at the needle could also be generated if the end of the discharge pipework is submerged below liquor level in the feed tank.

When the sample needle terminates at, or below, the center line B of the sample 'Tee' side arm 19, air bubbles, drawn from the sample bottle during evacuation, are carried away from the 'Tee' in the liquor flow. When however the needle terminates above the side arm, the air bubbles collect in the top limit of the 'Tee', position A of FIG. 2, and are drawn into the sample bottle at the expense of liquor during the sampling stage of the cycle. This effect causes lower sampling rates measured with the needle terminating above the side arm of the sample 'Tee' than those with the needle terminating below it, even though the vacuum generated in the sample bottle is approximately the same in each case.

The increase in sample rate obtained with the 60 mm long, 0.85 mm ID needle fitted with a 75 mm long, 6 mm ID extension, over that obtained with a 128 mm long, 0.85 mm ID needle, is almost certainly due to the reduced pressure drop through the increased diameter needle extension.

The length of pipework on the discharge side of the sample 'Tee', required to enable a reasonable sampling rate to be obtained, does not necessarily have to be incorporated in the vertical pipe run but could be horizontal or formed into a coil if space limitations apply.

Thus it is possible to use an RFD to provide liquor to a sample point and also to evacuate the sample bottle. The position of the sample needle should be such that its lower end terminates at, or preferably below, the center line of the sample 'Tee' side arm 19. The sample rate per stroke of the RFD depends on the length of the pipework in the discharge line from the sample 'Tee', and also on the RFD drive pressure. Provided that the RFD drive time is sufficiently long to ensure that a significant length of the discharge pipework downstream from the sample 'Tee' runs full of liquor, no advantage is gained in increasing drive time.

Air or liquor was not ejected from the sample needle when the sample bottle was absent from the needle, with the RFD drive pressure varying between 550 and 827 mbar, if the needle 22 or needle extension 40 terminated below the center line of the side arm of the 'Tee', and no turbulence or regions of high pressure were generated in the sample 'Tee'. To this effect the geometry of the 'Tee' piece should be smooth and free from sudden changes of cross-section and the discharge pipework should not be so long as to produce high back-pressures at the 'Tee'. The discharge pipework should terminate at a break pot and not be submerged in the liquor of the feed tank, since this can also result in high back pressures with the possibility of air or liquor ejection from the needle.

I claim:

1. Sampling apparatus comprising a source of liquid to be sampled, a sample station elevated with respect to the source, a first pipe for delivery of liquid from the source to the sampling station, a second pipe extending from the sampling station, the first and second pipes respectively forming longer and shorter arms of a syphon, a needle at the sample station having one end in a flow connection between the first and second pipes, a bottle at the sample station for receiving sample liquid through the needle, and means for causing delivery and return flows of liquid in the first pipe from the source to the sample station so that on the delivery flow liquid flows past the one end of the needle to the second pipe to reduce the pressure in the bottle and on the return flow a syphon effect is created and liquid flows from the second pipe past the one end of the needle to the first pipe and sample liquid flows through the needle into the bottle.

2. Apparatus as claimed in claim 1, comprising a T-piece connection at the sampling station, the leg to the T being connected to receive liquid delivered to the station, one branch of the T being connected to the second pipe, and the other branch being closed by a plug through which the needle extends, said one end of the needle in the T-piece being at or below the level of the center line of the leg.

3. Apparatus as claimed in claim 2, in which the length of needle in the T-piece has a greater internal diameter than the needle in the bottle.

4. Sampling apparatus as claimed in claim 1, in which said means for causing delivery comprises a reverse flow diverter, and means for operating the reverse flow diverter.

* * * * *